United States Patent
Macgregor et al.

(10) Patent No.: US 9,410,886 B2
(45) Date of Patent: Aug. 9, 2016

(54) APPARATUS AND METHOD FOR GENERATING LIGHT PULSES FROM LEDS IN OPTICAL ABSORPTION GAS SENSORS

(75) Inventors: Calum John Macgregor, Ayr (GB); Desmond Robert Gibson, Argyll & Bute (GB)

(73) Assignee: GAS SENSING SOLUTIONS LTD., Cumbernauld (GB)

( * ) Notice: Subject to any disclaimer, the term of this patent is extended or adjusted under 35 U.S.C. 154(b) by 150 days.

(21) Appl. No.: 13/882,585

(22) PCT Filed: Oct. 28, 2011

(86) PCT No.: PCT/GB2011/052111
§ 371 (c)(1),
(2), (4) Date: Jul. 5, 2013

(87) PCT Pub. No.: WO2012/059744
PCT Pub. Date: May 10, 2012

(65) Prior Publication Data
US 2013/0271751 A1    Oct. 17, 2013

(30) Foreign Application Priority Data
Nov. 1, 2010 (GB) .................................. 1018417.4

(51) Int. Cl.
*G01N 21/00* (2006.01)
*G01N 21/61* (2006.01)
(Continued)

(52) U.S. Cl.
CPC .............. *G01N 21/61* (2013.01); *G01N 21/274* (2013.01); *G01N 21/3504* (2013.01); *G01J 11/00* (2013.01); *G01N 2201/0696* (2013.01); *G01N 2201/127* (2013.01); *G01N 2201/1211* (2013.01)

(58) Field of Classification Search
CPC ................. G01N 2201/0696; G01N 2201/12; G01N 2201/0624; G01N 21/3504; G01N 21/61; G01J 11/00
See application file for complete search history.

(56) References Cited

U.S. PATENT DOCUMENTS 4,071,298 A * 1/1978 Falconer ............ G01N 15/1459
356/301
4,166,961 A * 9/1979 Dam ................... A61M 1/1692
250/573

(Continued)

FOREIGN PATENT DOCUMENTS

CN    101040567    9/2007
CN    101688830    3/2010

(Continued)

OTHER PUBLICATIONS

D.D. Nelson, "Sub-part-per-billion detection of nitric oxide in air using a thermoelectrically cooled mid-infrared quantum cascade laser spectrometer", Aug. 21, 2002.*

(Continued)

*Primary Examiner* — Michael A Lyons
*Assistant Examiner* — Maurice Smith
(74) *Attorney, Agent, or Firm* — Nixon & Vanderhye P.C.

(57) ABSTRACT

An optical absorption gas sensor for detecting an analyte gas comprises a gas sample receiving chamber, at least one light emitting diode (LED) and a photodiode or other photosensor. A plurality of light pulses are generated by passing pulses of current through the at least one LED. The current through the at least one LED is measured a plurality of times during each pulse and taken into account when generating a compensated output signal. The transfer ratio between LED current and photodiode output signal is calculated a plurality of times during each pulse. An ADC measures the LED and photodiode currents alternately. The LED pulses are generated by inductor discharge flyback and the period of time for which current is supplied to the inductor prior to each pulse is selected so that the photodiode output current is at an optimal region within the input range of the ADC. At least the temperature of the at least one LED is measured and taken into account when generating the compensated output signal. Thus, rather than providing especially careful control of the LED pulses, the pulses are measured, enabling a simpler, lower power circuit which is tolerant of variations in temperature to be provided.

25 Claims, 3 Drawing Sheets

(51) Int. Cl.
  *G01N 21/27*    (2006.01)
  *G01N 21/3504*  (2014.01)
  *G01J 11/00*        (2006.01)

(56) References Cited

U.S. PATENT DOCUMENTS

| | | | |
|---|---|---|---|
| 4,190,836 A * | 2/1980 | Kimura et al. | 345/46 |
| 4,742,575 A | 5/1988 | Arita et al. | |
| 4,958,926 A * | 9/1990 | Bu-Abbud | H01S 5/06835 250/205 |
| 5,121,337 A * | 6/1992 | Brown | 702/28 |
| 5,261,415 A | 11/1993 | Dussault | |
| 5,477,853 A | 12/1995 | Farkas et al. | |
| 5,590,652 A | 1/1997 | Inai | |
| 5,697,011 A | 12/1997 | Kobayashi et al. | |
| 6,002,952 A * | 12/1999 | Diab | A61B 5/02416 600/310 |
| 6,114,700 A | 9/2000 | Blades | |
| 6,229,315 B1 * | 5/2001 | Briggs | 324/623 |
| 7,339,173 B2 | 3/2008 | Stein et al. | |
| 2002/0038081 A1 * | 3/2002 | Fein | A61B 5/14552 600/323 |
| 2004/0095184 A1 * | 5/2004 | Oka et al. | 327/478 |
| 2005/0082553 A1 | 4/2005 | Yamamoto et al. | |
| 2005/0269513 A1 | 12/2005 | Ianakiev et al. | |
| 2006/0176919 A1 * | 8/2006 | Nagasaka | H01S 5/042 372/38.02 |
| 2006/0192728 A1 * | 8/2006 | Kim | 345/46 |
| 2006/0197452 A1 * | 9/2006 | Zhang | 315/32 |
| 2008/0154103 A1 * | 6/2008 | LeMay | 600/323 |
| 2009/0072749 A1 * | 3/2009 | Saldana | 315/158 |

FOREIGN PATENT DOCUMENTS

| | | | | |
|---|---|---|---|---|
| DE | 42 16 085 | 12/1992 | | |
| EP | 0 992 094 | 9/2002 | | |
| EP | 0 864 180 | 7/2004 | | |
| GB | WO2009/119467 | * | 2/2009 | G01N 21/35 |
| JP | 60-210039 | 10/1985 | | |
| JP | 6-63032 | 3/1994 | | |
| JP | 7-199640 | 8/1995 | | |
| JP | 2002-236053 | 8/2002 | | |
| JP | 2005-129598 | 5/2005 | | |
| WO | 97/18460 | 5/1997 | | |
| WO | 2007/091043 | 8/2007 | | |
| WO | 2009/005799 | 1/2009 | | |
| WO | 2009/019467 | 2/2009 | | |
| WO | WO 2009/019467 | 2/2009 | | |

OTHER PUBLICATIONS

International Search Report for PCT/GB2011/052111 mailed Feb. 23, 2012.

Haigh et al. Applied Physics Letters vol. 90, 231116 (2007).

* cited by examiner

APPARATUS AND METHOD FOR GENERATING LIGHT PULSES FROM LEDS IN OPTICAL ABSORPTION GAS SENSORS

This application is the U.S. national phase of International Application No. PCT/GB2011/052111 filed 28 Oct. 2011 which designated the U.S. and claims priority to GB 1018417.4 filed 1 Nov. 2010, the entire contents of each of which are hereby incorporated by reference.

FIELD OF THE INVENTION

1. Background to the Invention

The invention relates to the field of optical absorption gas sensors which employ an LED (for example, an infra-red LED) as a source of light.

2. Background to the Invention

Optical absorption gas sensors include both a source of light and a detector of light (a photosensor). Light from the source is directed through a gas sample and detected by the photosensor. The concentration of an analyte gas in the gas sample can be determined from the absorption of light by the analyte gas. Typically, either the source will emit light predominantly within a wavelength range corresponding to absorption lines of the intended analyte, or the photosensor will be sensitive to light predominantly within a wavelength range corresponding to absorption lines of the intended analyte, either due to the inherent properties of the light sensitive transducer which is employed (e.g. a photodiode) or due to the presence of a wavelength filter which selects only light within a wavelength range including absorption wavelengths of the target analyte. Within this specification and the appended claims, light refers to electromagnetic radiation irrespective of wavelength and includes, for example, electromagnetic radiation in the infra-red region of the spectrum as this is a region within which many analyte gases have strong absorption lines.

Light emitting diodes (LEDs) are inexpensive and relatively energy efficient devices and so they are commonly employed as sources of light for optical absorption gas sensors, particularly devices which are intended to be small and low cost. For many applications, an LED with a peak emission wavelength in the infra-red region of the spectrum is suitable.

Typically, the current supplied to an LED in an optical absorption gas sensor is pulsed and, indeed, one of the advantages of LEDs is that they can be readily pulsed. There are several reasons why pulsed light sources are employed. Firstly, pulsing the source of light provides a signal at the detector which is similarly pulsed, and so which can be readily separated from noise and any background signal by known signal processing techniques, such as synchronous demodulation. Secondly, a pulsed source of light consumes less energy than a source which emits light continuously at the same peak power consumption. Thirdly, it is known to shape the pulses, to facilitate the measurement process. Furthermore, LEDs have maximum operating currents above which the LED would be damaged by the resulting heat were the LED operated continuously and pulsing allows higher maximum operating currents and therefore higher peak outputs of light than would otherwise be the case.

One complication is that the output from an LED is sensitive to temperature (amongst other factors). As the measured gas concentration is determined from the attenuation of light, small effects on LED output can have a substantial effect on the measured gas concentration. The temperature of the diode junction will vary not only with ambient temperature, but also with the pulse pattern, and within individual LED pulses. This presents a technical problem, as it is necessary to control or compensate in some way for this variation with temperature. Many photosensors are also sensitive to temperature, amongst other factors.

In order to obtain a high signal to noise ratio, it is generally preferable that the pulses of light be relatively short but of relatively high intensity. Due to the potential for damage by excessive heat there is a trade off between maximum current and therefore maximum peak emitted light intensity and the duration of pulses. However, known circuits to drive LEDs to provide short pulses of light, with a high signal-to-noise ratio and clear pulse shaping, require complex control electronics and consume a substantial amount of power.

Accordingly, the invention aims to provide an alternative optical absorption gas sensor which employs relatively short pulses of light generated by an LED, and thereby obtains accurate sensor output despite variations in LED temperature while minimising power consumption.

SUMMARY OF THE INVENTION

According to a first aspect of the present invention there is provided a method of operating an optical absorption gas sensor for detecting an analyte gas, the sensor comprising a gas sample receiving chamber, at least one light emitting diode (LED) and a photosensor (e.g. a photodiode) having an output signal (e.g. a current) sensitive to the amount of light received by the photosensor, the method comprising generating a plurality of pulses of light by passing a plurality of pulses of current through the at least one LED, and measuring the current through the at least one LED a plurality of times during each said pulse, and generating a compensated signal indicative of the concentration of an analyte gas in the gas sample receiving chamber taking into account both the photosensor output signal and the plurality of measurements of the current through the at least one LED.

One skilled in the art will appreciate that the current through the at least one LED can be measured by directly measuring the current or, for example, by measuring a potential difference related to the current, for example, by passing the current through a resistor and measuring the potential difference across the resistor.

The current through an LED is closely linked to the output of light by the LED and so, by measuring the current through the at least one LED a plurality of times during each pulse, features of the shape of the light pulse (variation in intensity with time) can be determined. Thus, rather than focussing only on controlling the shape of the light pulse, the invention involves measuring the shape of the light pulse, or related properties, during pulses and taking the measurements into account when determining the compensated signal. This avoids the requirement for complex electronics to precisely control the shape of each pulse, and therefore the cost and power consumption associated with complex pulse shaping circuits.

The output of light is typically a function of the current through an LED. Typically this is a linear function up to a threshold and non-linear thereafter, or non-linear across the majority or substantially all of the useful current range.

In order to increase the maximum light output which can be obtained with a broadly linear relationship to current, a plurality of LEDs may be employed. They may for example be connected in series or parallel. In this case, typically the current through each may be measured. The current through each LED of a plurality of LEDs may be measured independently and than each current measurement taken into account (for example, summed), or the current through a plurality of LEDs connected in series and/or parallel may be measured (e.g. the current into or out of a circuit comprising a plurality of LEDs connected in series and/or parallel). However, the method may comprise measuring a current through the at least one LED and calculating a value linked to light output through the at least one LED using a non-linear function, or a lookup table. This latter approach is especially helpful where the at least one LED may be pulsed to a current which is not a linear function of light output.

Preferably, the photosensor output signal (e.g. the current through a photodiode) is also measured a plurality of times during each said pulse. The plurality of measurements of the photosensor output signal may also be taken into account when generating the compensated signal.

Thus, by what is effectively sampling the current through the at least one LED a plurality of times during each pulse, information concerning the shape of each pulse (profile of light intensity versus time) can be obtained. This may, for example, enable a better estimate of the total light emitted by the at least one LED during a pulse than would be obtained by measuring current at a single instant, or by measuring e.g. peak current. Thus, the method may comprise estimating the total light output during a pulse from the measurements of current through the at least one LED a plurality of times during the pulse.

The current through the at least one LED and the photosensor output signal may be measured alternately (or simultaneously) during the plurality of pulses.

The current through the at least one LED may be measured using an analogue to digital converter (ADC). The ADC may measure the potential difference across a resistor through which the current through the at least one LED is passed. The photosensor output signal may be measured by an ADC. A single ADC may be used to measure the current through the at least one LED and the photosensor output signal, for example, alternately.

Preferably, the current through the at least one LED, and where applicable, the photosensor output signal, are measured at least 10 times or more preferably at least 20 times during each pulse.

The method preferably also includes the step of measuring the temperature of the at least one LED (and optionally also the temperature of the photosensor if the photosensor is sensitive to temperature, for example, if the photosensor is a photodiode). The measured temperature may be taken into account when generating the compensated signal. The amount of light generated per unit of current will vary with temperature and this enables the amount of light generated to be more accurately determined. A plurality of measurements of the temperature of the at least one LED may be made during each pulse. The said plurality of temperature measurements may be taken into account when generating the compensated signal.

The compensated signal may by a value indicative of (e.g. proportional to) the light received by the photosensor. The compensated signal may be a value indicative of (e.g. proportional to the logarithm of) the concentration of the analyte gas in the gas sample receiving chamber.

The method may comprise calculating the ratio of the measured current through the at least one LED to the photosensor output signal, at least once and typically a plurality of times during a pulse. For example, the ratio of the most recent, or average (e.g. mean) measured current through the at least one LED to the most recent, or average (e.g. mean) photosensor output signal (e.g. the current from a photodiode) may be calculated a plurality of times during a pulse. The said ratio may be used to calculated the compensated signal.

The method may comprise calculating a transfer ratio of the estimated total light output from the at least one LED during a pulse (obtained from the said current measurements) to the estimated total light received by the photodiode during the pulse (from the measurement of the photosensor output current), or a parameter related to the said transfer ratio. The said transfer ratio, or parameter related thereto, may be used to calculate the compensated signal.

The method may comprise carrying out a frequency domain analysis of a plurality of measurement of the measured current through the at least one LED and the photosensor output signal (e.g. the current from a photodiode). For example, the method may comprise generating the pulses with a known frequency and calculating a parameter related to the energy of the measured current through the at least one LED and/or the photosensor output signal in one or more frequency bands, for example, a frequency band including the fundamental frequency (the frequency of the pulses) and one or more frequency bands including harmonics of the fundamental frequency (e.g. several consecutive harmonics starting from the first harmonics, e.g. first harmonic, second harmonic and third harmonic).

The pulses of current through the at least one LED may be generated by switching off a current source to an inductor and directing (the resulting) current from the inductor through at least one LED (and typically one or more other components such as a resistor, and typically also a switch or further diode to prevent reverse current flow through the at least one LED).

It may be that one or more properties of an LED current pulse, for example, the maximum current during a pulse or total charge passed through the at least one LED during a pulse, are selected depending on one or more of the measurements of the current through the at least one LED carried out during an earlier LED current pulse. The one or more measurements may, for example, be the peak current through the at least one LED during an earlier pulse, or the ratio of the current through the at least one LED to the photosensor output signal from one or more measurements during an earlier pulse.

The one or more properties may be selected by determining the period of time for which current is supplied by a switching device (such as a transistor or a MOSFET) to an inductor operatively connected to (e.g. connected in series with) the at least one LED before the supply of current to the inductor is restricted (typically stopped) by the switching device. The period of time for which current is supplied to the inductor determines the total amount of energy stored in the inductor and the magnitude of the current then supplied by the inductor to the at least one LED.

It may be that one or more properties of an LED current pulse is selected depending on one or more measurements of the photosensor output signal, for example to control where the photosensor output signal is relative to the dynamic range of an ADC measuring the photosensor output signal. The one or more properties may be selected by determining the period of time for which current is passed through an inductor before the current source is restricted (typically stopped) to drive current from the inductor through the at least one LED.

The one or more properties of an LED current pulse may be selected to compensate for a measured property, e.g. the temperature of the at least one LED or the photosensor. The one or more properties of an LED current pulse may be selected to regulate the magnitude of the photosensor output signal, for example, to keep the photosensor output signal, or an amplified signal derived therefrom, within a preferred region of the dynamic range of an ADC, e.g. to minimise quantisation effects or to avoid the photosensor output signal, or an amplified signal derived therefrom, from exceeding the dynamic range of an ADC.

In addition to the said pulses during which the current through the at least one LED is measured a plurality of times (and where applicable the photosensor output signal is measured a plurality of times), there may also be pulses during which the current through the at least one LED is not measured a plurality of times (and/or where applicable the photosensor output signal is measured a plurality of times).

According to a second aspect of the invention there is provided an optical absorption gas sensor comprising a gas sample receiving chamber, at least one light emitting diode (LED) and a light detector (such as a photodiode) having an output signal (e.g. a current) sensitive to the amount of light received by the photosensor, an LED control circuit configured to generate a plurality of pulses of light in a measurement mode of the optical absorption gas sensor by passing a plurality of pulses of current through the at least one LED, measuring device configured to measure the current through the at least one LED a plurality of times during each said pulse, and a compensation module configured to output a compensated signal indicative of the concentration of an analyte gas in the gas sample receiving chamber, taking into account both the light detector output signal and the plurality of measurements of the current through the at least one LED.

The sensor to measure the current through the at least one LED may be a current sensor. However, the sensor to measure the current through the at least one LED may be a potential difference sensor configured to measure a potential difference which depends on the current through the at least one LED, for example, the potential difference across a resistor (typically a resistor connected in series with the at least one LED) through which the current from the at least one LED is passed.

Preferably, the gas sensor comprises a measuring device to measure the photosensor output signal (e.g. a current sensor to measure the current through a photodiode) a plurality of times during each pulse. The same measuring device may measure both the current through the at least one LED and the photosensor output signal. The or each said measuring device may be an ADC. A switch may be provided to alternately connect the sensor to an output of the at least one LED and an output of the photosensor (typically through one or more other components, such as an amplifier).

The optical absorption gas sensor preferably also comprises one or more temperature sensors and the compensation module takes into account the one or more sensed temperatures. A temperature sensor may measure the temperature of the at least one LED. A separate temperature sensor may measure the temperature of the photosensor. Temperature may be measured by measuring a parameter related to temperature, such as the forward voltage, $V_F$, across the LED (and/or photodiode where the photosensor is a photodiode).

The LED control circuit may be configured to determine one or more properties of the LED pulses controlled by the LED control circuit responsive to one or more of the measurements of the current through the at least one LED and/or one of the more of the measurement of the photosensor output signal carried out during an earlier LED current pulse. Typically, the one or more properties of the LED pulses are determined by controlling the period of time for which current is supplied to the inductor.

The LED control circuit may comprise an inductor connected in series with the at least one LED (and typically one or more other components such as a resistor). The LED control circuit may be operable to supply current to the inductor and then to restrict (e.g. stop) the supply of current to the inductor, thereby causing current to flow through the at least one LED. The LED control circuit may be configured to select the current supplied to the inductor and/or the period of time for which the current is supplied to the inductor responsive to one or more of the measurement of the current through the at least one LED and/or one of the more of the measurement of the photosensor output signal carried out during an earlier LED current pulse.

The optical absorption gas sensor may comprise a frequency domain analysis module operable to analyse of a plurality of measurement of the measured current through the at least one LED and the photosensor output signal (e.g. the current from a photodiode). For example, the optical absorption gas sensor may be operable to generate the pulses with a known frequency and comprise a frequency domain analysis module operable to calculate a parameter related to the energy of the measured current through the at least one LED and/or the photosensor output signal in one or more frequency bands, for example, a frequency band including the fundamental frequency (the frequency of the pulses) and one or more frequency bands including harmonics of the fundamental frequency (e.g. several consecutive harmonics starting from the first harmonic, e.g. first harmonic, second harmonic and third harmonic). The frequency domain analysis module may be an electronic module. The frequency domain analysis module may comprise computer program code executed by a processor.

The optical absorption gas sensor is preferably adapted to selectively measure the concentration of a specific analyte gas, for example, by selection of one or more of the output light spectrum of the at least one LED, the spectral range over which the photosensor is sensitive and or the presence of a filter, such as a band pass filter, within the optical path (e.g. covering the at least one LED or photosensor). The optical gas sensor may be adapted to detect an analyte such as carbon dioxide, carbon monoxide, methane, water vapour (to measure humidity) etc. by selecting the LED and photodiode to generate and detect light specifically at one or more wavelengths where the analyte gases absorb strongly.

The at least one light emitting diode (and photodiode where the photosensor is a photodiode) may each be formed from a narrow band gap III-V material indium aluminium antimonide material ($(In_{1-x})Al_xSb$), grown on a gallium arsenide (GaAs) substrate, the doping of which is chosen to tune the band gap to cause the light emitting diode to emit light of a narrow wavelength range corresponding to a wavelength at which the intended analyte (e.g. gaseous carbon dioxide) absorbs strongly. The formation of suitable light emitting diodes and photodiodes are disclosed in EP 0 864 180, EP 0 992 094, and in Haigh, M. K. et al., Applied Physics Letters, vol. 90, 231116 (2007), the contents of each of these documents being incorporated herein by virtue of this reference.

Optional features presented in respect of the first or second aspect of the invention above are optional features of either the first or second aspect of the invention.

The invention also extends in a third aspect to an optical absorption gas sensor comprising a gas sample receiving chamber, at least one light emitting diode (LED) and a light detector having an output signal sensitive to the amount of light received by the photosensor, and a control circuit configured to cause the optical absorption gas sensor to operate according to the method of the first aspect of the invention. The control circuit may comprise a computer readable medium (e.g. a memory, such as a ROM or PROM) storing program code and a processor (e.g. a microcontroller) operable to execute the program code.

DESCRIPTION OF THE DRAWINGS

An example embodiment of the present invention will now be illustrated with reference to the following Figures in which.

DETAILED DESCRIPTION OF AN EXAMPLE EMBODIMENT

Figure 1:
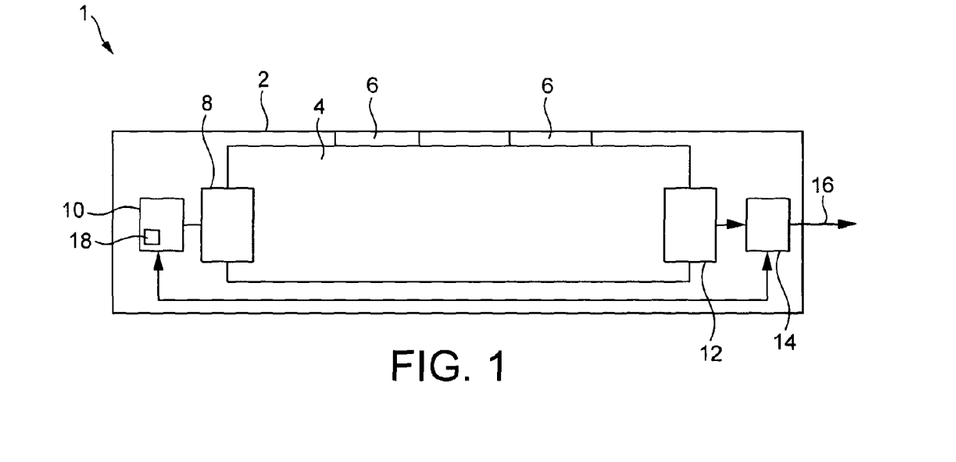
FIG. 1 is a schematic diagram of an optical absorption gas sensor.

With reference to FIG. 1, an optical absorption gas sensor 1 has a body 2 defining a gas sample chamber 4, into which a gas sample can pass by diffusion through one or more apertures 6. A light emitting diode 8 functions as a light source, and is driven by an LED control and pulse measurement circuit 10. A photodiode 12 functions as a photosensor, and has an output current dependent on the light which falls on the photodiode junction. The current from the photodiode is amplified and processed by a control and compensation circuit 14 including a microcontroller, which implements a compensation function and thereby provides a compensated signal through an output 16. The control and compensation circuit also receives information concerning the shape of LED pulses and controls the LED control circuit.

The gas sample chamber may have any of a large number of configurations known to those skilled in the art, and typically includes a reflective inner surface, so that light from the LED may be reflected one or more times between the LED and a photodiode. The LED and photodiode may be located adjacent to each other, or further apart. The optical arrangement is selected so that the attenuation of light within a wavelength characteristic of a target analyte affects the current from the photodiode. Thus, the LED may have a defined range of output wavelengths, the photodiode may be sensitive to a defined range of output wavelengths and/or a wavelength band pass filter may be provided.

The LED control and pulse measurement circuit includes a temperature sensing circuit 18. The temperature sensing circuit determines the temperature of the photodiode by measuring the forward voltage, $V_f$, across the photodiode respectively. Suitable circuits for determining temperature by measuring the forward voltage are disclosed in WO 2009/019467 (Gas Sensing Solutions Limited) and an example is shown in FIG. 2.

Figure 2:
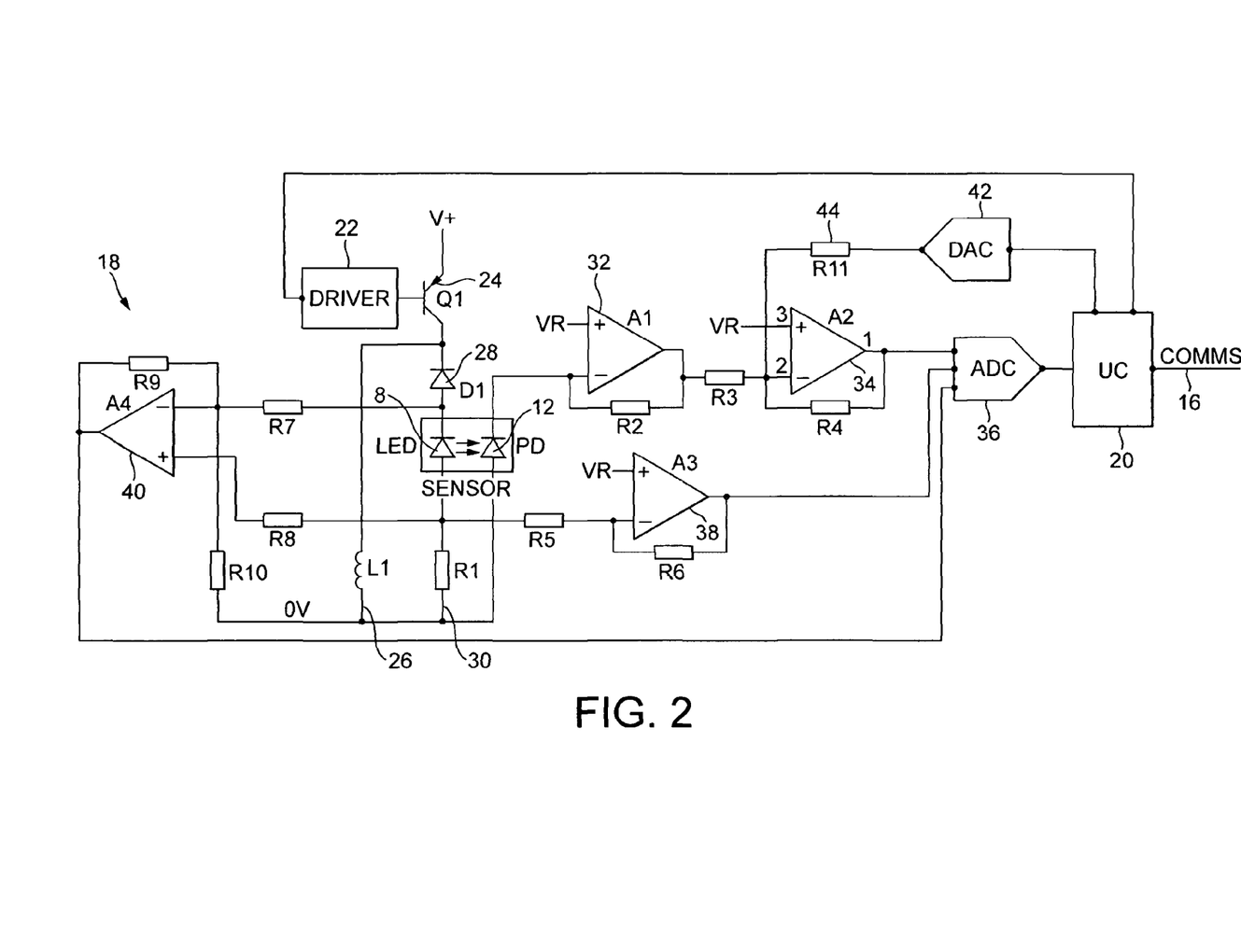
FIG. 2 is a circuit diagram for operating an optical absorption gas sensor.

FIG. 2 illustrates a circuit for controlling the gas sensor, including both the LED control and pulse measurement circuit, LED temperature measurement circuit and a microcontroller 20 which executes program code stored on a computer readable medium, such as a ROM, and functions as the compensation module. The system power supply, V+ is typically between 2.7 and 5 V. The microcontroller 20 controls the overall operation of the gas sensor, and can communicate with external devices through a serial data interface 16. The LED 8 is driven by a inductor flyback converter controlled through a driver circuit 22 which is in turn controlled by the microcontroller which can precisely set the on and off times for a switching device in the form of a transistor 24.

The transistor 24 is switchable to provide current to an inductor 26 under the control of the driver circuit. The inductor is connected in parallel with a circuit branch including the LED, a second diode 28 (which functions to prevent reverse current flow through the LED, which is potentially substantial for infra-red LEDs which have very high reverse voltage leakage currents), and a resistor 30 provided to enable the current through the LED to be measured by virtue of the resulting potential difference across the resistor 30.

The circuit also includes the photodiode 12 and a photodiode output signal amplifier chain having first and second photodiode signal amplifiers 32 and 34 in series. An ADC 36 receives the output from the second amplification amplifier as an input.

The ADC has two further inputs. One input is the output signal from an amplifier 38 configured to measure the potential difference across resistor 30. The other input to the ADC is an output from a differential amplifier 40 which amplifies the LED forward voltage, for use in measuring the temperature of the LED.

The reference voltage $V_R$ received as an input by amplifiers 32, 34 and 38 is selected to bias these amplifiers to a suitable working point. The value of the reference voltage is not critical, although it must be stable during any given measurement. It may, for example, be at the middle of the temperature range of the ADC. To facilitate the operation of the photodiode amplifier chain, a digital to analogue converter 42 is also provided, under the control of the microcontroller, to introduce a selectable offset to the second amplifier of the photodiode amplifier chain via a resistor 44, so that the output from the second amplifier stage can be biased to an optimum level.

The photodiode amplifier chain is DC coupled, so that it may be turned on or off very quickly either by switching its power supply or using amplifier chips having shutdown capability. The first amplifier 32 of the photodiode amplifier chain should be a low noise device, and the voltage gain of the photodiode amplifier chain should be very high as the output current from a photodiode is small.

Figure 3:
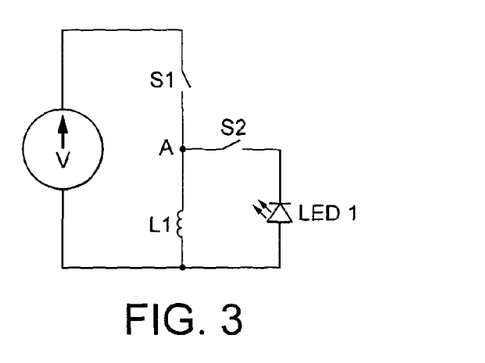
FIG. 3 is a schematic diagram of the principle behind the inductor driven mechanism for generating light pulses.
Figure 4:
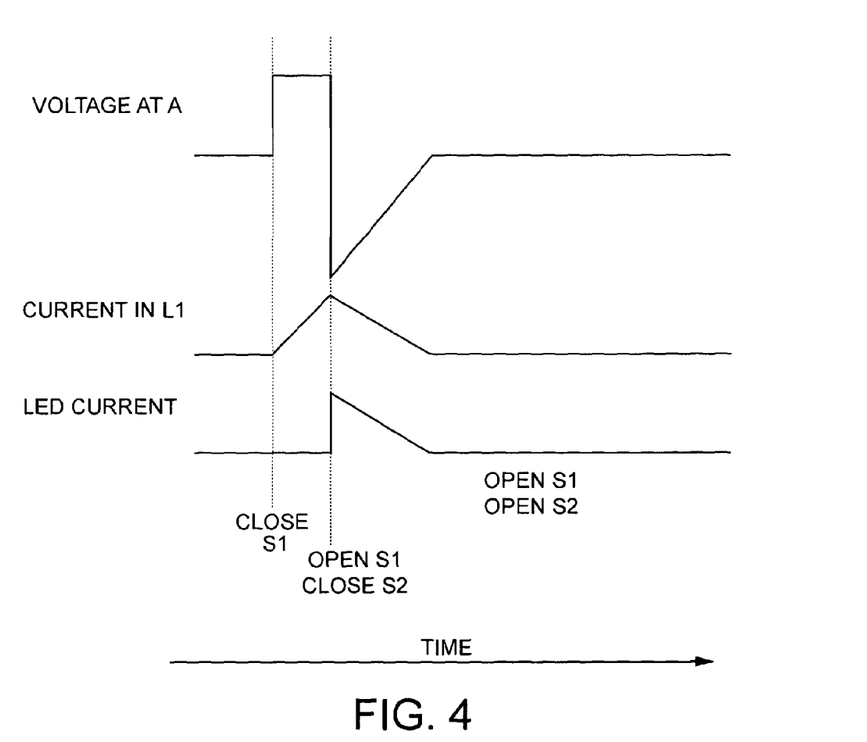
FIG. 4 is a graph of the variation in voltage at A, inductor current and LED current with time.

FIG. 3 is a schematic diagram of the principle behind the inductor driven mechanism for generating light pulses and FIG. 4 is a graph of the variation in voltage at A, inductor current and LED current with time. A power supply provides a voltage source, V. S1 is a switch (transistor, MOSFET etc.) which is switchable to open and close a circuit extending between the power supply and inductor L1. S2 is a further switch (a diode in the example embodiment, but S2 may also be a transistor, MOSFET etc.). LED1 is the light emitting diode (or in some embodiments a plurality of LEDs connected in series or parallel). Before each pulse, both switches are open. S1 is closed, the voltage V1 is applied to the inductor. The current through the inductor therefore increases at a constant rate (dI/dt=V/L). S1 is then opened and S2 closed. The inductor then drives point A negative and current flows through the inductor, S2 and the LED until the energy stored in the inductor has been expended. S2 can then be opened if need be. For a fixed inductor and supply voltage, the energy stored in the inductor and thus the duration of the pulse is determined by the period of time for which switch S1 is open.

In operation, in the circuit of FIG. 2, the microcontroller controls the driver circuit to execute a measurement cycle comprising a plurality of light pulses. For each pulse the transistor (functioning as switch S1) is switched on and current begins to flow into the inductor. The current increases linearly with time. After a period of time determined by the controller, the transistor is switched off. As a result, the voltage at the transistor collector is driven negative by the inductor which then acts to maintain the current flow through the inductor as the magnetic field in the inductor is discharged. The resulting current flows through the LED and resistor 30, causing the LED to generate light and the resistor to develop a potential difference proportional to the current through the LED. This continues until the potential difference across the inductor drops below the turn on threshold for the LED. (In an alternative embodiment, a MOSFET switched by the potential at the junction of L1 and D1 is employed as the switching device).

The number of pulses in each measurement cycle, and the duration of the pulses, is typically selected according to the performance of the ADC, the amplifier chain and other considerations. For example, fifty pulses of 20 μs duration may be applied to the LED. The inductance of the inductor is chosen to obtain a suitable pulse length and peak current. For example, the inductor may have an inductance of 200 μH and the peak current may be around 300 mA. However, these values would depend very much on the properties of the or each LED.

This circuit does not carefully control the shape of individual pulses and the precise value of the current in the LED will vary according to many factors, including the supply voltage (which will often drop by a small amount after each pulse within a measurement cycle), the inductance of the inductor, and the period of time for which the transistor is switched on for each pulse. The invention compensates for this by measuring the current pulse in the LED and using the resulting measurement when calculating a compensated output signal. The measurements are also used to control the period of time for which current is supplied to the inductor during subsequent pulses.

The ADC alternately measures the LED current via the LED output current amplifier 38 and then the photodiode current via first and second photodiode amplifiers 32, 34. For example, a twelve bit ADC may be employed making around 1,000,000 samples per second The CPU receives the data measured by the ADC and processes it, firstly to separate signal from noise and background using a synchronous demodulation procedure, known to one skilled in the art, and to otherwise filter and condition the resulting signal. The microcontroller then calculates the transfer ratio between the LED light output and the light measured by the photodiode. For example, it may estimate the total light output from the LED during a pulse by calculating a function and/or reading a lookup table to determine a measure of light output at the time when each LED current was measured from the respective LED current, and integrating these values throughout the pulse to estimate the total light output. The light measured by the photodiode can also be calculated by integrating the photodiode current during the pulse. Both of these values can be scaled and corrected as required, and may be integrated over many pulses. The ratio of the two can then be used as the output signal, indicative of the concentration of analyte gas.

In some embodiments, a plurality of readings (typically at least 32) of LED current and photodiode current may be taken during each pulse and all of the various measurements, for each of many pulses (typically at least 8 or at least 16) may be processed simultaneously, using a frequency domain analysis algorithm, such as a Fourier transform, Fast Fourier Transform, Discrete Fourier Transform or the Goertzel algorithm. In an example embodiment, the pulses are generated at a continuous and known rate. The repetition rate of the pulses and the size of the inductor are chosen to obtain a desired pulse duty cycle, typically between 30 and 50%. The shape of the pulses is somewhere between a square and a triangle and so most of the energy in the pulse train is contained within the fundamental, first, second and third harmonics of the pulse frequency. The sampled values of the LED current and the photodiode current, obtained using the ADC can be transformed using a Fourier transform. From the resulting signal, the energy in the fundamental and the harmonics can be calculated. Typically, the total number of samples is a power of 2 to simplify subsequent calculations, e.g. there may be 512, 1024 or 2048 samples. There should also be an exact number of pulses in the total sample period, which means in practice that the number of pulses will be a power of 2, typically 8, 16 or 32. From the Fourier transform, the amplitude of the fundamental and the harmonics, and therefore the energy of these frequency bands, can be readily calculated by standard methods. The ration of the total energy in the LED current in these frequency bands to the energy in the photodiode current in these frequency bands provides a measurement of the transfer ratio. This technique allows the signals to be both filtered and averaged in one mathematical operation. Typically, the Fourier transform is calculated by a computationally efficient method known to those skilled in digital signal processing, such as Fast Fourier Transform or the Goertzel algorithm This approach is also advantageous as a difficulty with pulse by pulse measuring is that the power supply usually drops a little with each pulse. Whilst methods exist to prevent this they are costly in terms of parts and power consumption. If each pulse is different the transfer ratio should be calculated for each individual pulse and this requires the time at which each pulse starts and stops to be known very accurately. This can mean that the signal processing requires a greater bandwidth than is otherwise desirable and increases the overall noise. Accordingly, the frequency domain analysis provides a useful approach for cost and time efficient data processing.

Furthermore, the microcontroller dynamically varies the period of time for which the transistor is switched on from one current pulse to the next. The transfer ratio varies significantly with temperature and so by adjusting the period of time for which the transistor is on, the processor can keep the amplitude of the photodiode signal from becoming too large at low temperatures, or too small at high temperatures, for accurate readings to be obtained. This ensures that ADC quantisation noise does not adversely affect the system at high temperatures, and enables the dynamic range of the ADC to be appropriately employed.

Differential amplifier 40 provides a measurement of the forward voltage of the LED. This can be used to establish the temperature of the LED as the forward voltage is a function of temperature. A relationship between forward voltage and temperature can be stored in a lookup table. The controller may, for example, cause a low current pulse or pulses to be applied to the LED at the beginning of a measuring cycle (each cycle into the product of pulses) to measure the temperature in the LED. The output from the differential amplifier at that time is processed by the ADC.

As a result, shorter LED pulses can be employed than would be the case if the shape of each pulse had to be carefully controlled. Furthermore, the use of the inductor enables peak LED current to be determined independently of supply voltage. Thus, short high amplitude pulses can be employed. This in turn improves the signal to noise ratio of the measuring system as a whole (photodiode, ADC and microcontroller) because, although shorter pulses require a larger bandwidth, thermal noise (which is the dominant source of noise in the amplifier chain) increases with the square root of bandwidth but the photodiode output signal increases linearly. If, for example, peak LED current was increased from 50 mA to 200 mA and the duration of each pulse reduced by a factor of four, the noise would only increase by a factor of two. In practice, LEDs have series resistance which reduces the efficiency as the current increases so that gain in signal to noise ration is less than would be anticipated. Nevertheless, the net effect is an improvement in signal to noise ratio.

The ability to dynamically adjust LED current and offset also reduces ADC noise effects. The invention also has the benefit that measurements may be carried out very quickly. For example, it may be possible to carry out an entire measurement in less than 10 ms, including taking a temperature measurement, measuring LED and photodiode current during fifty light pulses, and processing the resulting data. The procedure may therefore be repeated and averaged and still provide a rapid result, although each repetition increases the total power output.

The circuit illustrated in FIG. 2 also has the advantage of being energy-efficient in comparison with simple circuits for driving LEDs employing a resistor in series with the LED, or an active current source. Furthermore, most such circuits require power supplies well in excess of 3 V. A suitable switching regulator can of course convert a 3 V supply at a higher voltage although this would reduce efficiency.

The sensor is tolerant of a reasonable temperature differential between LED and photosensor, enabling the LED and photosensor to be spaced apart, for example, at opposite ends of a waveguide.

In an alternative embodiment, a plurality of LEDs are provided, connected in series or parallel, and the current through the plurality of LEDs is measured. This increases the range of light output over which the current is a roughly linear function of light output, or at least sufficiently sensitive to light output to enable light output to be estimated with reasonable accuracy.

In some embodiments, a resistor is placed in series with the inductor (L1) and the potential difference across that series resistor in order to measure the current through the inductor. This enables the micro controller to regulate the pulses which are generated to ensure that the current in the inductor does not exceed a threshold.

Further variations and modifications may be made by one skilled in the art within the scope of the invention herein disclosed.

The invention claimed is:

1. A method of operating an optical absorption gas sensor for detecting an analyte gas, the sensor comprising a gas sample receiving chamber, at least one light emitting diode (LED) and a photosensor having an output signal sensitive to the amount of light received by the photosensor, the method comprising:
generating a plurality of pulses of light by passing a plurality of pulses of current through the at least one LED, and measuring the current through the at least one LED a plurality of times during each said pulse of light to thereby measure information concerning the shape of the light pulse, and
generating a compensated signal indicative of the concentration of an analyte gas in the gas sample receiving chamber taking into account both the photosensor output signal and the measured information concerning the shape of the light pulse.

2. The method according to claim 1, wherein the photosensor output signal is also measured a plurality of times during each said pulse.

3. The method according to claim 2, wherein the plurality of measurements of the photosensor output signal are also taken into account when generating the compensated signal.

4. The method according to claim 1, wherein the current through the at least one LED and the photosensor output signal are measured alternately during the plurality of pulses of light.

5. The method according to claim 1, wherein the current through the at least one LED is measured using an analogue to digital converter (ADC).

6. The method according to claim 1, wherein an ADC is used to measure the current through the at least one LED and the photosensor output signal.

7. The method according to claim 1, wherein the temperature of the at least one LED is measured and the measured temperature is taken into account when generating the compensated signal.

8. The method according to claim 1, wherein the method comprises calculating the ratio of the measured current through the at least one LED to the photosensor output signal, at least once during a pulse.

9. The method according to claim 1, wherein the method comprises carrying out a frequency domain analysis of a plurality of measurement of the measured current through the at least one LED and the photosensor output signal.

10. The method according to claim 1, wherein the method comprises generating the pulses with a known frequency and calculating a parameter related to the energy of the measured current through the at least one LED and/or the photosensor output signal in one or more frequency bands.

11. The method according to claim 1, wherein the pulses of current through the at least one LED are generated by switching off a current source to an inductor and directing current from the inductor through the at least one LED.

12. The method according to claim 1, wherein one or more properties of an LED current pulse are selected depending on one or more of the measurements of the current through the at least one LED carried out during an earlier LED current pulse.

13. The method according to claim 12, wherein the said one or more properties are selected by determining the period of time for which current is supplied by a switch to an inductor operatively connected to the at least one LED before the supply of current to the inductor is restricted by the switch.

14. The method according to claim 12, wherein one or more properties of an LED current pulse is selected depending on one or more measurements of the photosensor output signal.

15. The method according to claim 12, wherein the one or more properties of an LED current pulse are selected to compensate for a measured property of the at least one LED or the photosensor.

16. The method according to claim 1, wherein the current through the at least one LED is measured by passing the current through a resistor and measuring the potential difference across the resistor.

17. An optical absorption gas sensor comprising:
a gas sample receiving chamber,
at least one light emitting diode (LED),
a light detector having an output signal sensitive to the amount of light received by the light detector,
an LED control circuit configured to generate a plurality of pulses of light in a measurement mode of the optical absorption gas sensor by passing a plurality of pulses of current through the at least one LED, a sensor configured to measure the current through the at least one LED a plurality of times during each said pulse of light to thereby measure information concerning the shape of the light pulse, and a computer processor executing a program stored in a non-transitory storage medium configured to output a compensated signal indicative of the concentration of an analyte gas in the gas sample receiving chamber, taking into account both the light detector output signal and the measured information concerning the shape of the light pulse.

18. The optical absorption gas sensor according to claim 17, wherein
the gas sensor comprises a sensor to measure the light detector output signal a plurality of times during each pulse.

19. The optical absorption gas sensor according to claim 17, comprising an ADC to measure both the current through the at least one LED and the light detector output signal.

20. The optical absorption gas sensor according to claim 19, wherein
the LED control circuit comprises an inductor operatively connected to the at least one LED and is operable to supply current to the inductor and then to restrict the supply of current to the inductor, thereby causing current to flow through the at least one LED.

21. The optical absorption gas sensor according to claim 20, wherein
the LED control circuit is configured to select the current supplied to the inductor and/or the period of time for which the current is supplied to the inductor responsive to one or more of the measurement of the current through the at least one LED and/or one of the more of the measurement of the light detector output signal carried out during an earlier LED current pulse.

22. The optical absorption gas sensor according to claim 17, wherein
the optical absorption gas sensor also comprises one or more temperature sensors and the computer processor takes into account the one or more sensed temperatures.

23. The optical absorption gas sensor according to claim 17, wherein
the LED control circuit is configured to determine one or more properties of the LED pulses controlled by the at least one LED control circuit responsive to one or more of the measurements of the current through the at least one LED and/or one of the more of the measurement of the light detector output signal carried out during an earlier LED current pulse.

24. The optical absorption gas sensor according to claim 17, wherein
the computer processor is configured to perform frequency domain analysis to analyze a plurality of measurement of the measured current through the at least one LED and the light detector output signal.

25. An optical absorption gas sensor comprising:
a gas sample receiving chamber,
at least one light emitting diode (LED),
a light detector having an output signal sensitive to the amount of light received by the light detector, and
a control circuit configured to cause the optical absorption gas sensor to operate according to the method of operating an optical absorption gas sensor for detecting an analyte gas, the sensor comprising a gas sample receiving chamber, at least one light emitting diode (LED) and a photosensor having an output signal sensitive to the amount of light received by the photosensor, the method comprising:
generating a plurality of pulses of light by passing a plurality of pulses of current through the at least one LED, and measuring the current through the at least one LED a plurality of times during each said pulse of light to thereby measure information concerning the shape of the light pulse, and
generating a compensated signal indicative of the concentration of an analyte gas in the gas sample receiving chamber taking into account both the photosensor output signal and the measured information concerning the shape of the light pulse.

* * * * *